(12) United States Patent
Im et al.

(10) Patent No.: US 9,376,223 B2
(45) Date of Patent: Jun. 28, 2016

(54) LIQUID CONTAINER HAVING VACUUM PUMPING DEVICE

(75) Inventors: Se Chul Im, Incheon (KR); Bang Bin Im, Gyeonggi-do (KR)

(73) Assignee: Yonhee Chemical Co., Ltd., Gyeonggi-Do (KR)

( * ) Notice: Subject to any disclaimer, the term of this patent is extended or adjusted under 35 U.S.C. 154(b) by 642 days.

(21) Appl. No.: 13/884,870

(22) PCT Filed: Nov. 7, 2011

(86) PCT No.: PCT/KR2011/008429
§ 371 (c)(1),
(2), (4) Date: Jun. 11, 2013

(87) PCT Pub. No.: WO2012/064062
PCT Pub. Date: May 18, 2012

(65) Prior Publication Data
US 2013/0255830 A1 Oct. 3, 2013

(30) Foreign Application Priority Data

Nov. 12, 2010 (KR) .................. 10-2010-0112511

(51) Int. Cl.
| | |
|---|---|
| *B65B 1/04* | (2006.01) |
| *B65B 3/12* | (2006.01) |
| *B65D 81/20* | (2006.01) |
| *A61M 5/178* | (2006.01) |
| *B65B 3/00* | (2006.01) |

(52) U.S. Cl.
CPC .............. *B65B 3/12* (2013.01); *B65D 81/2015* (2013.01); *B65D 81/2038* (2013.01); *A61M 5/1782* (2013.01); *B65B 3/003* (2013.01)

(58) Field of Classification Search
CPC ...... B65B 3/003; B65B 3/12; B65D 81/2015; B65D 81/2038; A61M 5/1782
USPC ..................................................... 141/27, 65
See application file for complete search history.

(56) References Cited

U.S. PATENT DOCUMENTS

2013/0160891 A1* 6/2013 Vassallo .................. B65B 3/003
141/27

FOREIGN PATENT DOCUMENTS

KR 100875906 B1 12/2008

*Primary Examiner* — Jason K Niesz
(74) *Attorney, Agent, or Firm* — Alston & Bird LLP (57) ABSTRACT

Provided is a liquid container having a vacuum pumping device, which includes: a housing having a lower portion which is opened by means of an opening or closing control to be exposed to the atmosphere and an upper portion having a mounting hole so that a space is formed therein; an inner container having a cylinder chamber provided at an upper portion thereof to allow a liquid to flow in or out and a liquid store area connected to a lower portion of the cylinder chamber to change a volume according to an amount of liquid therein, the cylinder chamber being coupled to the mounting hole of the housing so that the inner housing is detachably mounted in the housing for refilling; a syringe unit coupled to or separated from the cylinder chamber to suck the liquid from the inner container and discharge the sucked liquid outwards; and an elastic cap mounted to the cylinder chamber, the elastic cap being closed in advance when the syringe unit is inserted into the cylinder chamber and opened later when the syringe unit sucks the liquid after the syringe unit is inserted into the cylinder chamber, so that the liquid is discharged while keeping a sealed state. If the liquid container having a vacuum pumping device of the present disclosure is used, the elastic cap may be easily manufactured due to its simple design and may keep its sealing force even though it is used repeatedly. Further, since the movement of a membrane may prevent even a minimum air from flowing into a filling chamber of the liquid store area while the syringe unit is being inserted, it is possible to prevent the solution from being contaminated.

20 Claims, 10 Drawing Sheets

LIQUID CONTAINER HAVING VACUUM PUMPING DEVICE

CROSS-REFERENCE TO RELATED APPLICATIONS

This application is a national stage application filed under 35 U.S.C. 371 of International Application No. PCT/KR2011/008429, filed Nov. 7, 2011, which claims priority from Korean Patent Application No. 10-2010-0112511, filed Nov. 12, 2010, each of which is incorporated by reference herein in its entirety.

TECHNICAL FIELD

The present disclosure relates to a liquid container having a vacuum pumping device, and more particularly, to a liquid container having a vacuum pumping device, which allows the vacuum pumping device to be attached to or detached from the liquid container by means of a half turn and also allows the liquid contained in the container to be easily taken off and used by an amount required, in a state the container keeps a vacuum state.

BACKGROUND ART

Generally, various kinds of containers using a sprayer form or having a vacuum pumping device are used so that a cosmetic product or detergent in a liquid or gel state may be easily taken off and used. In particular, in case of a solution which should not contact oxygen, a vacuum pumping device is used to minimize a contact between the solution and oxygen, and the solution is contained in a container provided with a vacuum pump which is used for taking off the solution when necessary. Such a vacuum pumping device is disclosed in Korean Patent Registration No. 10-875906. Korean Patent Registration No. 10-875906 discloses that a cylinder and a piston are provided at a handle to take off a content from the container, and the content is discharged to a desired point by using the piston. In particular, a housing cap mounted to the top of the container and a cylinder detachably mounted to the housing cap are coupled in a threaded pattern.

However, if the above liquid container having a vacuum pumping device is used, since the cylinder is coupled and separated in a threaded pattern, the cylinder should be manipulated to make at least one turn, namely several turns. Therefore, whenever the liquid container is used, the locking state of the threaded coupling should be repeatedly adjusted, and the user should make repeated turns in a clockwise or counterclockwise direction, which is very cumbersome to use. In addition, an elastic cap with a complicated design is used for opening or closing the neck portion of the container, which is not easily fabricated. Moreover, if the elastic cap is opened or closed repeatedly, its elastic force deteriorates, and therefore the degree of sealing deteriorates as time goes, which results in introduction of air or alien substances. Further, when it is intended to discharge a content by pushing the piston, since the maximum static friction force between the piston and the cylinder is higher than a driving frictional force between the piston and the cylinder, the piston is strongly pressed when the piston is actually operated. Therefore, the content filled in the cylinder, particularly the content with low viscosity, is ejected under too strong pressure, which causes the content to be discharged more than required.

Therefore, in order to solve such problems, there is a need to develop a liquid container having a vacuum pump device, which may be easily manufactured due to a simple piston design, may be isolated from an external air regardless of use time by using an elastic cap, and may prevent the air from penetrating therein while the vacuum pump is inserted.

DISCLOSURE

Technical Problem

The present disclosure is directed to providing a liquid container having a vacuum pumping device, which allows a syringe unit to be easily coupled to or separated from the container by adopting a half turn manner and is capable of preventing an external air from penetrating therein so that a solution contained may not be contaminated for a long time.

Technical Solution

In one general aspect, the present disclosure provides a liquid container having a vacuum pumping device, which includes:

a housing having a lower portion which is opened by means of an opening or closing control to be exposed to the atmosphere and an upper portion having a mounting hole so that a space is formed therein;

an inner container having a cylinder chamber provided at an upper portion thereof to allow a liquid to flow in or out and a liquid store area connected to a lower portion of the cylinder chamber to change a volume according to an amount of liquid therein, the cylinder chamber being coupled to the mounting hole of the housing so that the inner housing is detachably mounted in the housing for refilling;

a syringe unit coupled to or separated from the cylinder chamber to suck the liquid from the inner container and discharge the sucked liquid outwards; and an elastic cap mounted to the cylinder chamber, the elastic cap being closed in advance when the syringe unit is inserted into the cylinder chamber and opened later when the syringe unit sucks the liquid after the syringe unit is inserted into the cylinder chamber, so that the liquid is discharged while keeping a sealed state.

According to an embodiment of the present disclosure, the syringe unit may be coupled to or separated from the cylinder chamber by means of a turn of 90° to 180°.

In addition, a protrusion may be formed in a space of the mounting hole of the housing, a protrusion coupling unit shaped corresponding to the protrusion may be formed at the upper end of the cylinder chamber, and the cylinder chamber may be fixed in the housing by means of coupling between the protrusion of the housing and the protrusion coupling unit of the cylinder chamber.

Here, the cylinder chamber may include a rotational pressing guide formed by cutting from the upper end of the cylinder chamber with a slope with respect to the longitudinal direction thereof, the rotational pressing guide having a hooking projection formed at a lower terminal thereof to prevent the syringe unit from bouncing in the longitudinal direction, and a guide protrusion guided by the rotational pressing guide may be further formed at the outer circumference of the syringe unit.

In addition, the protrusion coupling unit may be formed in plural at the cylinder chamber and include a first protrusion coupling unit located above a point eccentric from the center of the hooking projection toward the rotational pressing guide, the protrusion may be connected in plural to the housing and include a first protrusion contacting the first protrusion coupling unit, and the first protrusion may include a coupling surface contacting the first protrusion coupling unit and a slip surface oriented toward the housing, and the slip surface may be formed so that a distance to the syringe unit is shorter as being closer to the coupling surface.

In addition, the syringe unit may include:

a cylinder unit having the guide protrusion formed at the outer circumference of a tube-shaped cylinder body;

a piston unit mounted in the cylinder unit; and a coupling unit formed between the piston unit and the cylinder unit, wherein the piston unit may have a piston rod vertically movable along the piston guide unit and a piston head coupled to the lower end of the piston rod.

In addition, the cylinder unit may include:

the cylinder body;

an inlet/outlet tube connected to one end of the cylinder body and having a diameter smaller than or equal to that of the cylinder body;

a hydraulic pressure control valve coupled to one end of the cylinder body to control a hydraulic pressure of the liquid so that the liquid flowing into the cylinder body is not abruptly discharged out; and the guide protrusion formed at the outer circumference of the cylinder body, wherein the hydraulic pressure control valve may be made of elastic material with a plate shape and have a first inlet/outlet hole formed with an arc shape at a location spaced apart from the center of the hydraulic pressure control valve and a second inlet/outlet hole formed at the center of the hydraulic pressure control valve.

In addition, a barrier may be connected to one end of the cylinder body to protrude in the longitudinal direction of the cylinder unit, and the first inlet/outlet hole may be located at an upper portion of the barrier.

In addition, an inner diameter of the cylinder body may be one to ten times of an inner diameter of the inlet/outlet tube.

In addition, a grip having a diameter greater than the piston rod may be connected to the upper end of the piston rod, and a vertical length of the grip may be 15 mm to 35 mm.

In addition, the coupling unit may include:

a piston guide for limiting an upward movement range of the piston unit; and an auxiliary ring member located at a lower portion of the piston unit.

In addition, the piston unit may be inserted into the piston guide and the auxiliary ring member, an inner diameter of the piston guide may be smaller than an outer diameter of the piston head, and an outer diameter of the piston head vertically sliding in the auxiliary ring member may be greater than an inner diameter of the lower end of the auxiliary ring member.

In addition, the piston guide may include:

a flat flange having a piston insert hole; and a guide tube vertically connected downwards from the piston insert hole of the flange so that the piston unit is inserted therein.

In addition, a guide part may be formed at the guide tube to protrude into the guide tube, a piston guide groove may be concavely formed at the outer circumference of the piston unit in the vertical longitudinal direction, and the guide part may be inserted and coupled into the piston guide groove.

In addition, a rubber ring member for sealing the auxiliary ring member may be coupled between the lower end of the guide tube and the auxiliary ring member.

In addition, a rubber ring member for sealing the auxiliary ring member may be coupled to the outer circumference of the piston unit.

In addition, the elastic cap may include an insertion body into which a terminal of the syringe unit is inserted, and a channel opening/closing hole formed through the bottom surface of the insertion body, and a slit may be formed by cutting at the channel opening/closing hole so that the slit is opened when being pressed by the syringe unit.

In addition, the elastic cap may include an insertion body into which a terminal of the syringe unit is inserted, and a channel opening/closing hole formed through the bottom surface of the insertion body, and the channel opening/closing hole may have a membrane protruding upwards with a slant from the bottom surface of the elastic cap, and a cut portion formed through the membrane at an uppermost end of the membrane.

In addition, an elastic cap placing portion may be provided at a lower portion of the cylinder chamber located in the liquid store area so that the elastic cap is mounted thereto, and a channel control protrusion protruding upwards from the bottom surface and a discharge tube formed through the bottom surface of the elastic cap placing portion may be provided at the bottom surface of the elastic cap placing portion.

In addition, the bottom surface of the insertion body may be located at an upper portion of the discharge tube, and the elastic cap and the elastic cap placing portion may be coupled so that the channel control protrusion is inserted into the channel opening/closing hole, and the channel control protrusion may be formed spaced apart from the membrane.

Advantageous Effects

According to the present disclosure, the syringe unit may be coupled or separated by making a half turn, and a liquid may be discharged at a low speed from the syringe unit, which prevents the content from being discharged more than required at once and allows the content to be used little by little. Moreover, the elastic cap may be easily manufactured due to its simple design and may keep its sealing force even though it is used repeatedly. Further, since the movement of a membrane may prevent even a minimum air from flowing into a filling chamber in a liquid store area while the syringe unit is being inserted, it is possible to prevent the solution from being contaminated. In addition, since the inner container may be mounted or detached by just coupling or dissembling the finishing plate, easy refilling is ensured. Therefore, costs required for exchanging the container after the solution is used may be reduced, and the housing and the syringe unit may be recycled, which may reduce process time and costs and decrease environmental pollution.

BEST MODE

The present disclosure is directed to a liquid container having a vacuum pumping device, which may prevent a solution contained therein from contacting the air before being discharged out, different from a general case in which a solution in a container contacts the air just by opening the container containing the solution.

Mode for Invention

Hereinafter, the present disclosure will be described in detail based on embodiments. However, such embodiments are just for better understanding of the present disclosure, and the scope of the present disclosure is not limited thereto, as obvious to those having ordinary skill in the art.

Figure 1:
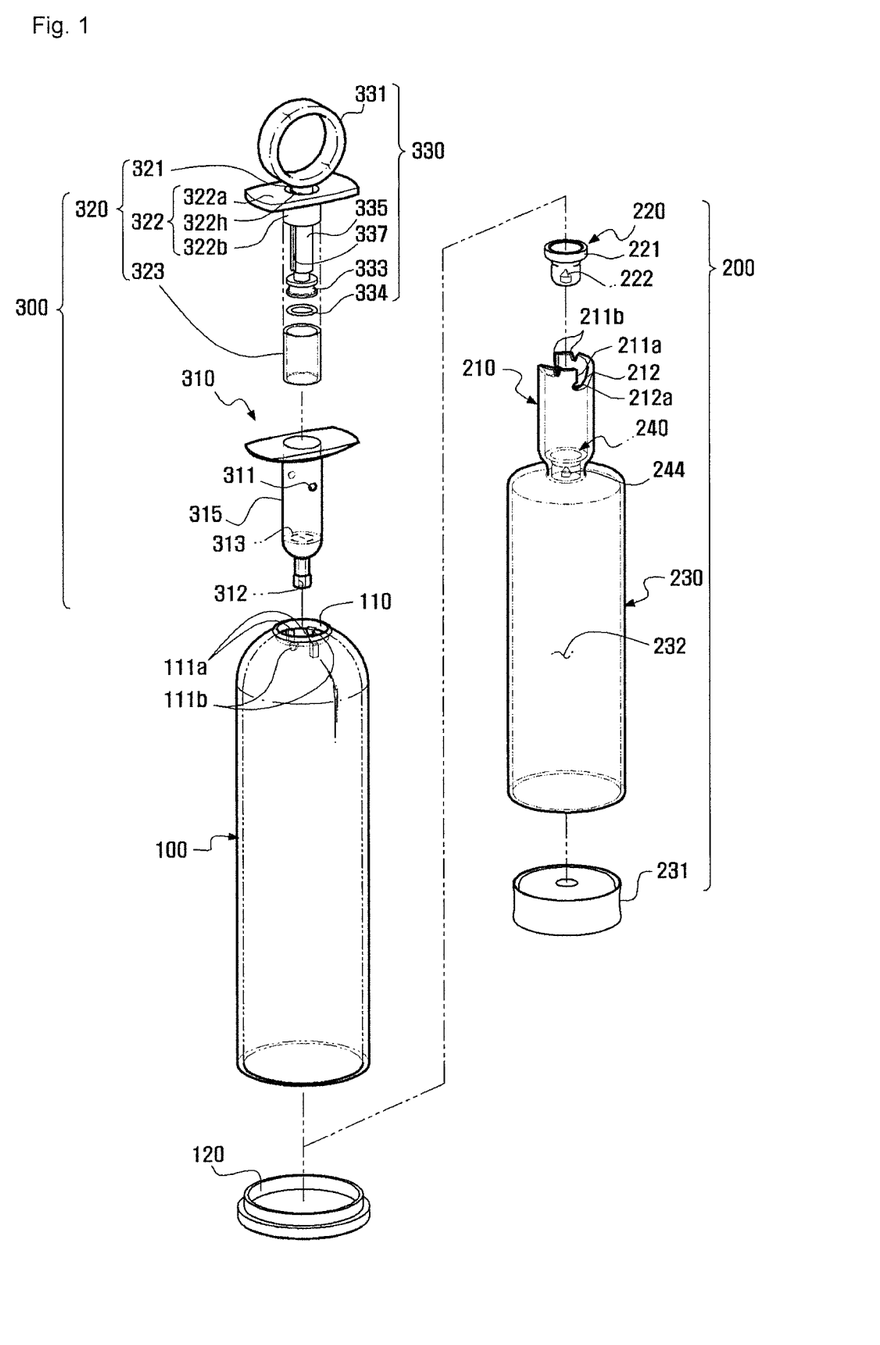
FIG. 1 is an exploded perspective view showing a liquid container having a vacuum pumping device according to an embodiment of the present disclosure.
Figure 2:
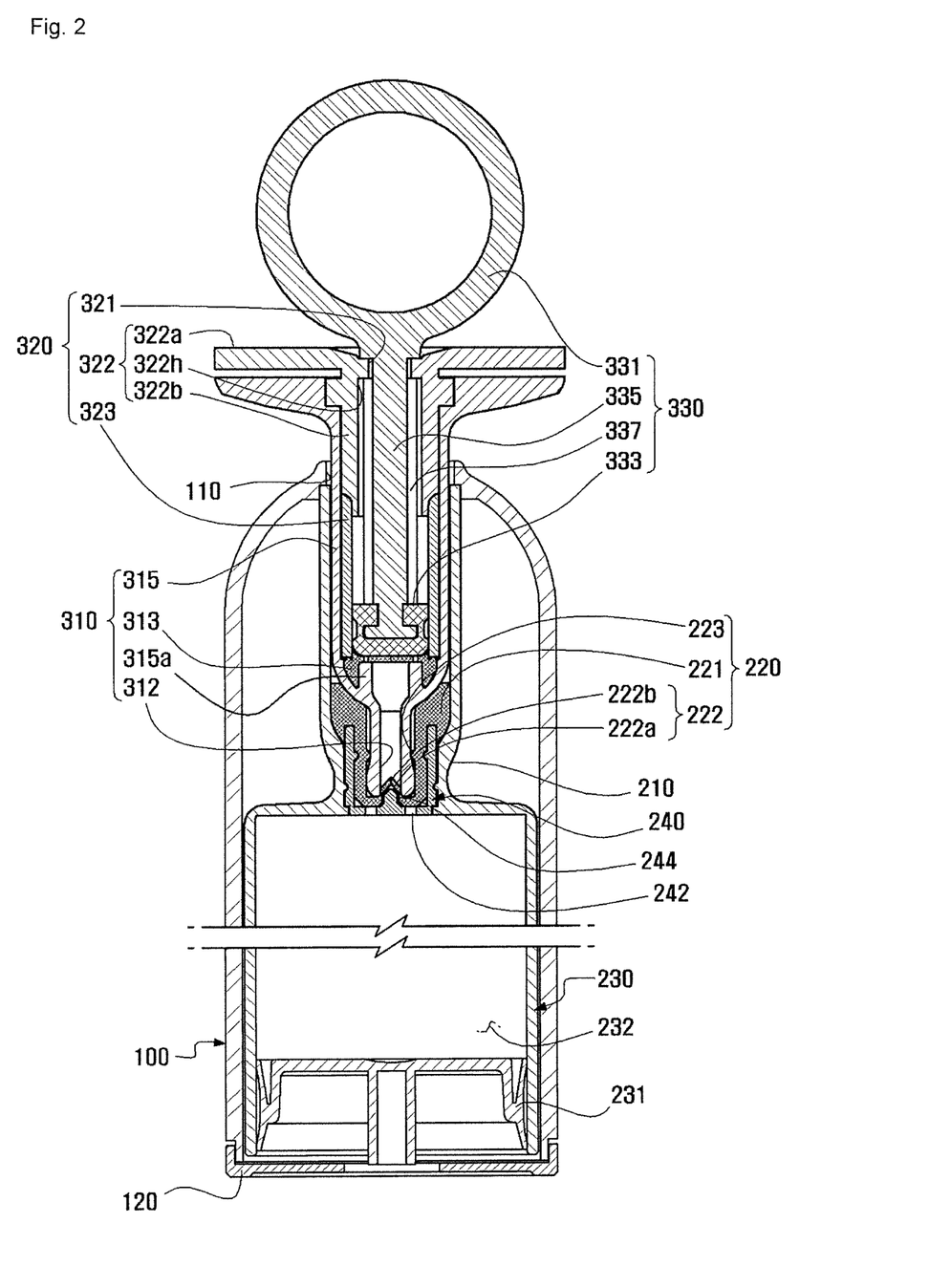
FIG. 2 is a cross-sectional view showing the liquid container having a vacuum pumping device according to an embodiment of the present disclosure.

FIG. 1 is an exploded perspective view showing a liquid container having a vacuum pumping device according to an embodiment of the present disclosure, and FIG. 2 is a cross-sectional view showing the liquid container having a vacuum pumping device according to an embodiment of the present disclosure.

The liquid container having a vacuum pumping device according to the present disclosure may be generally divided into a liquid container and a vacuum pumping device. The liquid container includes a housing 100 and an inner container 200 installed in the housing 100 to change its volume according to its content. In addition, the vacuum pumping device includes a syringe unit 300 coupled to or separated from the inner container 200 by means of a half turn to allow the content to be taken off, and an elastic cap 220 provided at the inner container 200 to keep sealing with the syringe unit 300.

A mounting hole 110 is formed at the upper portion of the housing 100, and the lower portion of the housing 100 is opened. The inner container 200 is inserted through the open portion of the housing 100 and then the open portion is closed by using a finishing plate 120. A protrusion is formed in the mounting hole 110 of the housing 100. If the protrusion is located at a protrusion coupling unit of the inner container 200, the inner container 200 is fixed in the housing 100. Here, in a state in which the finishing plate 120 is mounted, the height of the entire inside of the housing 100 is formed identical to the entire height of the inner container 200, so that the inner container may be fixed to the housing even though the protrusion coupling unit and the protrusion are not coupled in a complicated structure. In other words, the inner container 200 may be fixed in the housing 100 by limiting vertical or rotational movement. Here, the protrusion includes a first protrusion 111a and a second protrusion 111b, and the protrusion coupling unit includes a first protrusion coupling unit 211a coupled with the first protrusion 111a and a second protrusion coupling unit 211b coupled with the second protrusion 111b.

The inner container 200 which allows refilling may be generally divided into a liquid store area 230 storing a solution and a cylinder chamber 210 storing the syringe unit 300 and the elastic cap 220. At this time, an elastic cap 220 is mounted in the cylinder chamber 210 in order to prevent the air from flowing into the liquid store area 230. The liquid store area 230 has a filling chamber 232 in which a solution is stored. In other words, a sliding finishing plate 231 is inserted into the liquid store area 230, and a filling chamber 232 capable of storing a solution is formed in a region running from the upper surface of the liquid store area 230 to the upper surface of the sliding finishing plate 231. Since the filling chamber 232 maintains a volume due to the pressure of the solution, if the solution in the filling chamber 232 is discharged by the syringe unit 300, the sliding finishing plate 231 moves upwards by means of a vacuum pressure generated as much as the decreased volume of the solution, thereby decreasing the inner volume of the filling chamber 232. In other words, by slidably coupling the sliding finishing plate 231 in the liquid store area 230 as described above, the vertical length of the entire inner container 200 does not change. Therefore, even though the volume of the filling chamber 232 decreases, the inner container 200 may maintain its coupled state so that its location is fixed in the housing 100.

An elastic cap placing portion 240 is formed in the cylinder chamber 210, and the elastic cap 220 is located at the upper portion of the elastic cap placing portion 240. The elastic cap 220 prevents the air from flowing into the liquid store area 230, and the elastic cap 220 maintains a sealed state until a piston unit 330 of the syringe unit 300 is operated for discharging. Therefore, the solution contacts the air only when the solution is discharged out. In addition, in order to maintain the sealing, the elastic cap 220 may be made of elastic material such as silicon or rubber.

The syringe unit 300 may be generally divided into a piston unit 330 playing a role of a piston and a cylinder unit 310 and a coupling unit 320 playing a role of a cylinder. The piston unit 330 includes a piston rod 335, a piston head 333 coupled to the lower portion of the piston rod 335 and a grip 331 capable of easily adjusting a driving direction of the piston rod 335. The grip 331 is used for easily pulling the piston unit 330 inserted into the cylinder unit 310. Here, the grip 331 has a vertical length of 15 mm to 35 mm so that the grip 331 may be easily gripped. In other words, if the vertical length of the grip 331 is less than 15 mm, when gripping the grip 331, the fingers are excessively bent to surround the grip 331, which strains the finger joints. In addition, if the vertical length of the grip 331 is greater than 35 mm, when gripping the grip 331, the fingers are substantially not bent, and even though the fingers are bent to some extent to hole the grip 331, the gripping force of the fingers to move the piston rod 335 is not transmitted to the grip 331, which makes it impossible to adjust a location of the piston rod 335. Therefore, the grip 331 preferably has a vertical length of 15 mm to 35 mm. At this time, the grip 331 may have any shape such as a ring shape, a rectangular shape or a triangular shape, as long as its vertical length is in the range of 15 mm to 35 mm.

In addition, the piston head 333 is located at the lower end of the piston unit 330. The coupling unit 320 includes a piston guide 322 and an auxiliary ring member 323. The piston guide 322 includes a flat flange 322a and a piston insert hole 322h formed in the flange 322a. The piston rod 335 is inserted into the piston insert hole 322h. Here, in order to limit the moving path of the piston rod 335 to a vertical sliding direction, a tube-shaped guide tube 322b is formed to bend downwards from the piston insert hole 322h. A protruding guide part 321 may be protrusively formed at the piston insert hole 322h, namely above the guide tube 322b. At this time, by forming a piston guide groove 337 corresponding to the guide part 321 at the piston rod 335, the piston rod 335 may be operated to move more stably along the vertical sliding direction. The piston head 333 of the piston unit 330 has a limited driving range so that it may vertically slide particularly in the auxiliary ring member 323. In other words, as shown in FIG. 2, an outer diameter of the piston head 333 located at the lower end of the piston unit 330 is greater than an inner diameter of the guide tube 322b. Therefore, the piston head 333 may not slide in the guide tube 322b but slide only in the auxiliary ring member 323. The auxiliary ring member 323 is located at the lower portion of the guide tube 322b. The piston head 333 may limit the downward movement of the piston head 333 if the lower end of the auxiliary ring member 323 is formed to have an inner diameter smaller than the piston head.

The cylinder unit 310 may be generally divided into a cylinder body 315 and an inlet/outlet tube 312. The inlet/outlet tube 312 is inserted into the elastic cap 220 and communicates with the liquid store area 230 when the elastic cap 220 is opened. If a guide protrusion 311 formed at the outer surface of the cylinder body 315 is coupled with the rotational pressing guide 212 described above, the syringe unit 300 may be coupled with the inner container 200. The cylinder unit 310 and the coupling unit 320 may be fixed in various ways. For example, if a flat plate corresponding to the flange 322a of the coupling unit 320 is formed at the cylinder unit 310 and then adhered to the flange 322a, the cylinder unit 310 and the coupling unit 320 may be integrated as a single cylinder. By forming the coupling unit 320 in this way, the present disclosure may easily control a movement range of the piston head 333 and enhance the sealing, in comparison to a case in which a piston is directly installed at a cylinder.

Figure 3:
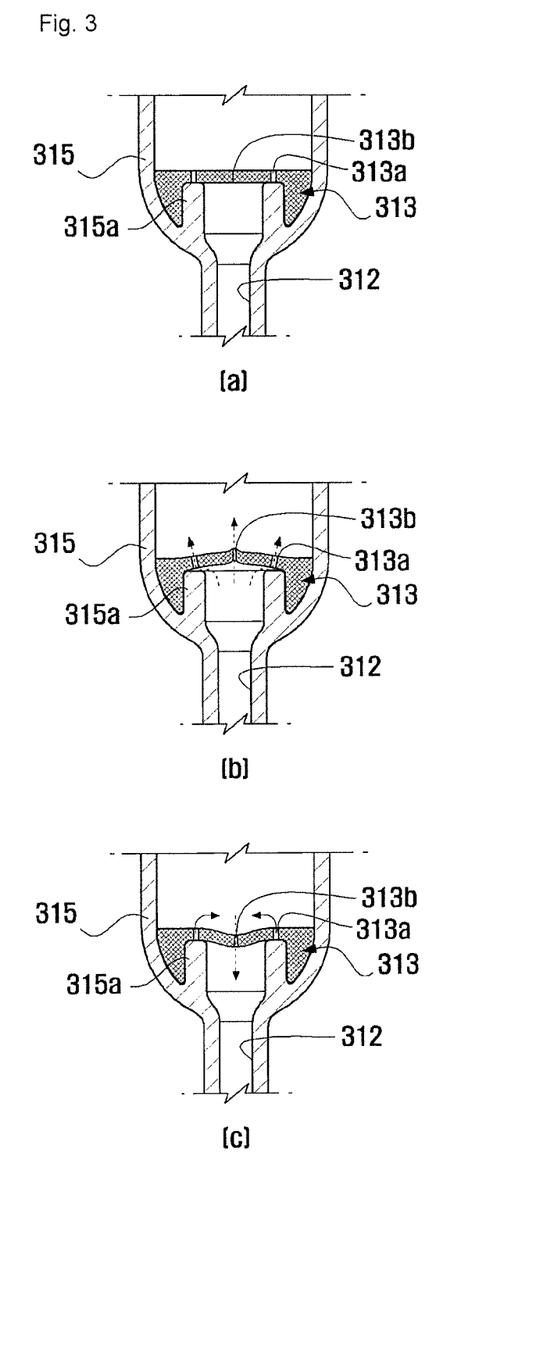
FIG. 3 is a cross-sectional view showing channel control valves according to various embodiments of the present disclosure.

FIG. 3 is a cross-sectional view showing channel control valves according to various embodiments of the present disclosure.

In order to prevent the content of the cylinder unit 310 from flowing out due to excessive pressure or speed, as shown in FIG. 3a, a hydraulic pressure control valve 313 is mounted to the cylinder body 315. The hydraulic pressure control valve 313 is made of easily elastically deformable material such as silicon or rubber. In addition, the hydraulic pressure control valve 313 has a shape of the inner section of the cylinder chamber 210, preferably a circular shape with a predetermined thickness. The hydraulic pressure control valve 313 has a plurality of circular inlet/outlet holes. At this time, the inlet/outlet holes are formed on a virtual arc and at the center of the hydraulic pressure control valve 313. In other words, among the plurality of inlet/outlet holes, first inlet/outlet holes 313a are formed in an arc space at locations spaced apart from the center of the hydraulic pressure control valve 313 by a predetermined distance, and second inlet/outlet holes 313b are formed at the center of the hydraulic pressure control valve 313. Here, the outer circumference of the hydraulic pressure control valve 313 may be shaped to be adhered to the inner shape of the cylinder unit 310, which enhances the sealing.

At this time, a barrier 315a is formed at one end of the cylinder body 315 to protrude in the longitudinal direction of the cylinder unit. Therefore, the hydraulic pressure control valve 313 may be formed so that the first inlet/outlet hole 313a is located above the barrier, which allows the hydraulic pressure to be controlled while the content flows in or out of the cylinder body 315. The hydraulic pressure control valve 313 may control the content to flow in or out in a following way. First, as shown in FIG. 3b, in case of moving the piston head 333 upwards to suck a solution into the syringe unit 300, the hydraulic pressure control valve 313 moves upwards along the solution, and the first inlet/outlet hole 313a closed by the barrier 315a is opened so that the solution may easily flow into the syringe unit through the inlet/outlet holes 313a, 313b. After that, in order to discharge the solution from the syringe unit 300, as shown in FIG. 3c, if the piston head 333 is pressed to move downwards, the hydraulic pressure control valve 313 moves downwards along the solution, and the first inlet/outlet hole 313a is closed by the barrier 315a, so that the solution is discharged only to the second inlet/outlet hole 313b cut into a slit shape. The second inlet/outlet holes 313b at the center of the hydraulic pressure control valve 313 are not formed at regular intervals but cut at once by using a cutting tool through the hydraulic pressure control valve 313. For this reason, the second inlet/outlet holes 313b may maintain a closed state when not in use. Therefore, it is prevented that the air flows into the syringe unit 300. For this reason, it is possible to prevent the solution in the syringe unit 300 from being contaminated. Moreover, since the second inlet/outlet hole 313b is opened only when a pressure is applied to the piston head 333 and the second inlet/outlet hole 313b is narrow even though it is opened, it is possible to prevent a large amount of solution from being discharged at once.

Figure 4:
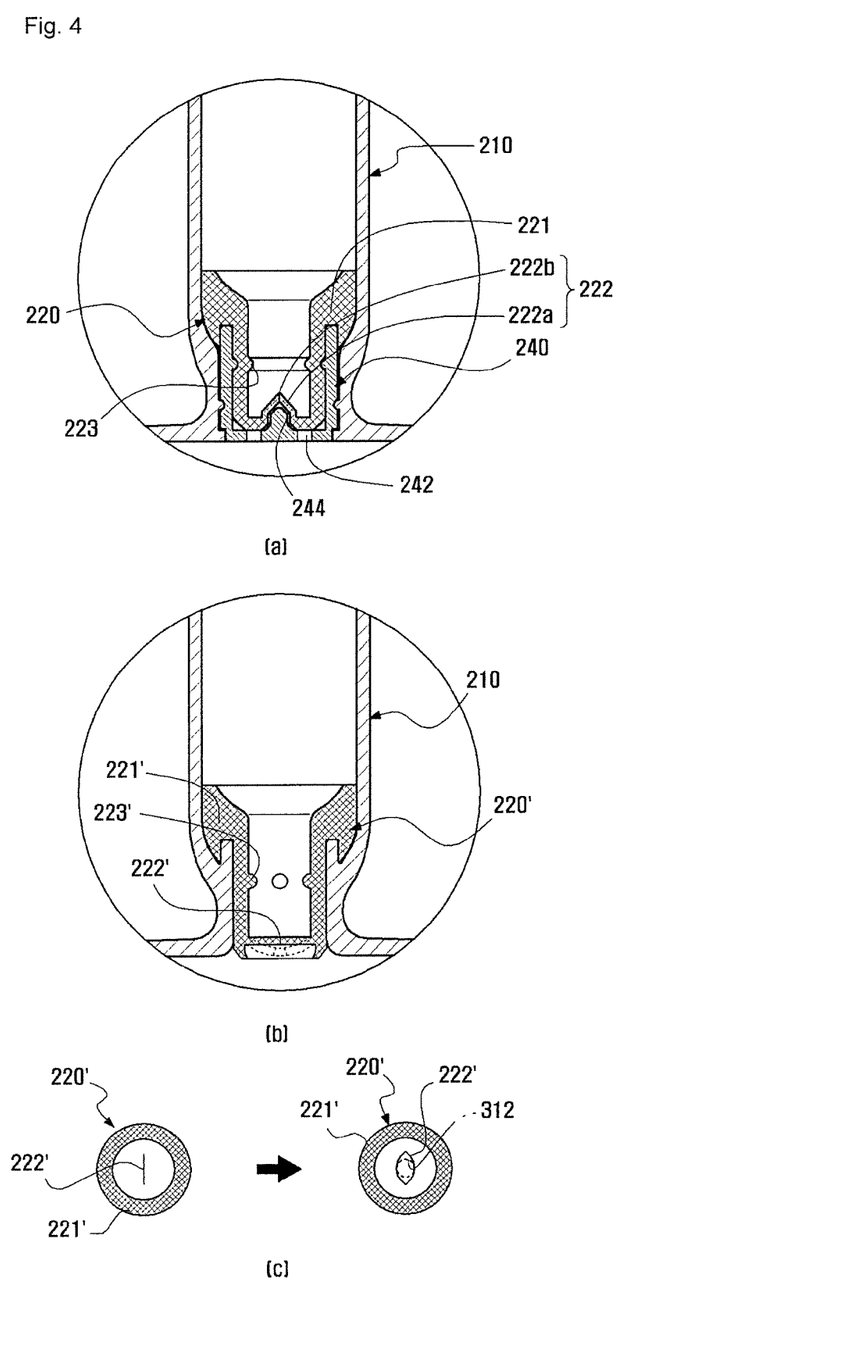
FIG. 4 is a cross-sectional view showing an elastic cap according to an embodiment of the present disclosure.

FIG. 4 is a cross-sectional view showing an elastic cap according to an embodiment of the present disclosure, and FIG. 5 is a cross-sectional view for illustrating an operating method of the elastic cap according to the embodiment of the present disclosure.

The elastic cap 220, 220' according to the present disclosure may be formed in various shapes, as shown in FIG. 4.

Here, the elastic cap 220, 220' is basically made of elastic material such as silicon or rubber into a container shape to maintain a sealed state. In particular, the upper portion of an insertion body 221, 221' of the elastic cap 220, 220' has an outer circumference compressed to the cylinder chamber 210 to maintain a sealed state and an inner circumference compressed to the cylinder unit 310 of the syringe unit 300 to maintain a sealed state. In addition, a guide protrusion 223, 223' is further formed on the inner circumference of the insertion body 221, 221' of the elastic cap 220, 220' at a location spaced apart from the bottom surface. The guide protrusion 223, 223' guides so that the lower end of the cylinder unit 310 is pressed perpendicular with respect to the bottom surface of the elastic cap 220, 220', so that a uniform pressure is applied to a channel opening/closing hole 222, 222'.

First, the elastic cap 220 according to an embodiment includes an insertion body 221 into which the inlet/outlet tube 312 is inserted, and a channel opening/closing hole 222 formed in the bottom surface of the insertion body 221. The channel opening/closing hole 222 is formed through the insertion body 221, and the solution in the liquid store area 230 is discharged through the channel opening/closing hole 222. The channel opening/closing hole 222 of the elastic cap 220 is divided into a membrane 222a and a cut portion 222b. The membrane 222a is connected to the insertion body 221 and protrudes from the bottom surface of the insertion body 221, preferably upwards with a slant. The cut portion 222b is formed through the membrane 222a, and the solution is discharged therefrom. Here, the cut portion 222b is particularly formed at the uppermost end of the membrane 222a.

The elastic cap 220 is placed on the elastic cap placing portion 240. In order to prevent introduction of the air more effectively when the elastic cap 220 primarily blocks the channel, locations where a discharge tube 242 and a channel control protrusion 244 are to be formed in the elastic cap placing portion 240 are taken into consideration. The channel control protrusion 244 is formed on the bottom surface of the elastic cap placing portion 240 and protrudes upwards from the bottom surface of the elastic cap placing portion 240 like a protrusion. In addition, the discharge tube 242 is formed through the bottom surface of the elastic cap placing portion 240. The channel control protrusion 244 may be located at the center of the elastic cap placing portion 240, particularly below the membrane 222a. At this time, the membrane 222a and the channel control protrusion 244 are spaced apart from each other by a predetermined distance, so that the solution may more easily move into the syringe unit 300 when the syringe unit 300 moves the piston head 333 upwards for sucking. In addition, the discharge tube 242 may be formed at a radially outward side from the channel control protrusion 244, and in particular, the bottom surface of the insertion body 221 is preferably located above the discharge tube 242. In other words, the cut portion 222b is not disposed directly above the discharge tube 242, but the bottom surface of the sealed insertion body 221 is located above the discharge tube 242. Therefore, even though the cut portion 222b is opened, the discharge tube 242 always communicates with the liquid store area 230 other than the period when the solution is discharged from the liquid store area 230, thereby preventing the air or the solution in the syringe unit 300 from flowing in again. The operation of the elastic cap 220 according to an embodiment of the present disclosure will be described in more detail with reference to FIG. 5.

The elastic cap 220' according to another embodiment of the present disclosure includes an insertion body 221' into which a terminal of the syringe unit 300 is inserted, and a channel opening/closing hole 222' formed through the bottom surface of the insertion body 221', as shown in FIGS. 4b and 4c.

The channel opening/closing hole 221' may be cut into a slit shape so as to be opened when being pressed by the syringe unit 300. If the slit-type channel opening/closing hole 222' is pressed by the lower end of the syringe unit 300, the channel opening/closing hole 222' is opened and communicates with the liquid store area 230. Here, the channel opening/closing hole 222' is formed in a straight shape, so that the inner container 200 may maintain a closed state at ordinary time. In other words, before the syringe unit is inserted, as shown in the left portion of FIG. 4c, the channel opening/closing hole 222' formed in the bottom surface of the insertion body 221' maintains a sealed state, and therefore the liquid store area 230 of the inner container 200 also maintains a sealed state. After that, if the syringe unit 300 is inserted, the terminal of the syringe unit 300 presses the bottom surface of the insertion body 221', which increases the area of the bottom surface of the elastic cap 220'. Therefore, the center portion of the channel opening/closing hole 222' formed like the bottom surface of the insertion body 221' as shown in the right portion of FIG. 4c is opened, and the inner circumference of the inlet/outlet tube 312 of the syringe unit 300 communicates with the filling chamber 232 of the liquid store area 230 so that the content in the filling chamber 232 may be sucked.

As described above, the elastic cap 220, 220' is compressed to the cylinder unit 310 and the cylinder chamber 210 and allows the channel opening/closing hole 222, 222' to be opened only by the insertion of the syringe unit 300 or the sucking operation, which may prevent the content in the filling chamber 232 from contacting the air and being contaminated.

Figure 5A:
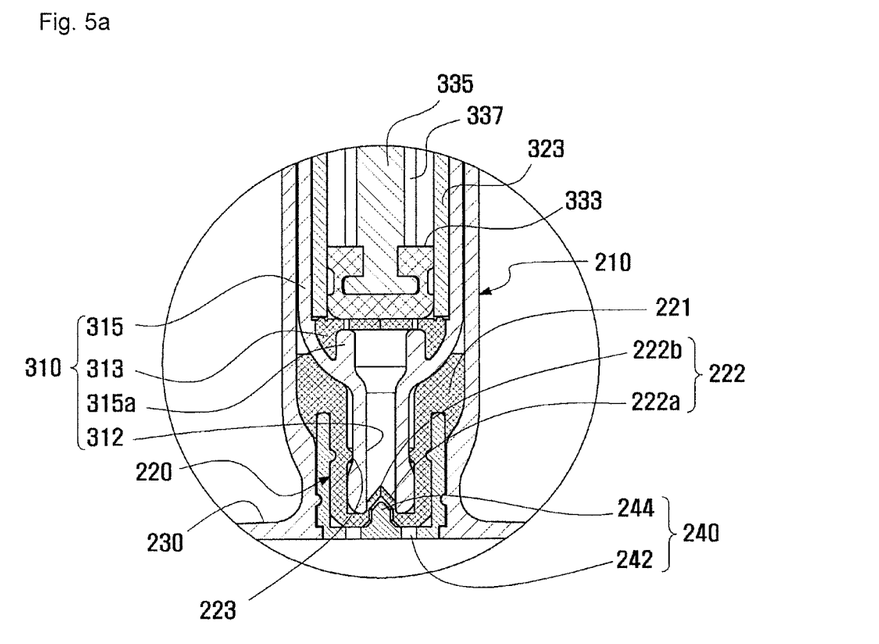
FIG. 5 is a cross-sectional view for illustrating an operating method of the elastic cap according to the embodiment of the present disclosure.
Figure 5B:
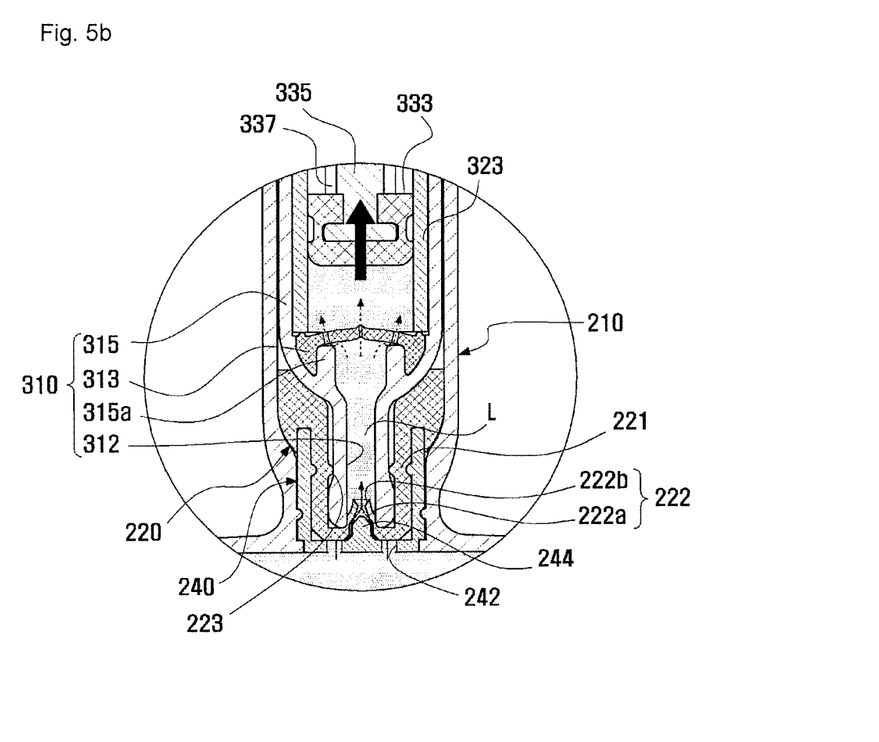
Figure 5C:
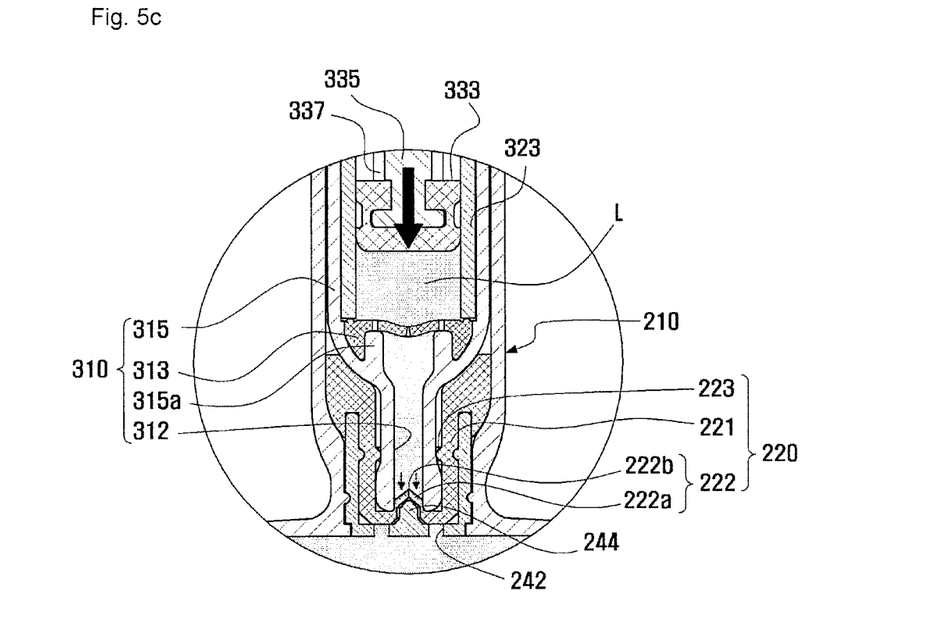

The cut portion 222b of the elastic cap 220 according to an embodiment of the present disclosure is opened or closed as follows. First, as shown in FIG. 5a, the syringe unit 300 is inserted into the cylinder chamber 210 so that the inlet/outlet tube 312 is placed on the insertion body 221 of the elastic cap 220. After that, as shown in FIG. 5b, if the piston head 333 is moved upwards, a vacuum pressure is generated and the solution in the liquid store area 230 moves upwards along the moving direction of the piston head 333. Here, the moving direction of the solution is steeper at a slope of the membrane 222a as shown in FIG. 5b, which makes the cut portion 222b be opened. Therefore, the elastic cap 220 is opened, and the solution is moved to the syringe unit 300. Here, regarding the movement of fluid in an opposite direction, the cut portion 222b of the elastic cap 220 is closed. In other words, as shown in FIG. 5c, if the piston head 333 is pressed in a state in which the solution remains in the syringe unit 300, the fluid moves downwards. Therefore, the slope of the membrane 222a becomes gentle, and the cut portion 222b is closed. At this time, even though the cut surfaces of the cut portion 222b are not arranged to face each other, it is possible to prevent the fluid from flowing into the liquid store area 230. In other words, if the fluid in the syringe unit 300 moves downwards, the pressure is applied to the membrane 222a in a downward direction, and therefore the membrane 222a comes into contact with the channel control protrusion 244 to close the moving passage of the fluid. Here, the fluid may be a solution L in the syringe unit 300 or the air introduced into the cylinder chamber 210 when the syringe unit 300 is mounted to the cylinder chamber 210. If the elastic cap 220 and the elastic cap placing portion 240 are formed as described above, the liquid store area 230 is closed other than a case in which the solution in the liquid store area 230 is discharged, thereby preventing the solution in the liquid store area 230 from being contaminated.

Figure 6:
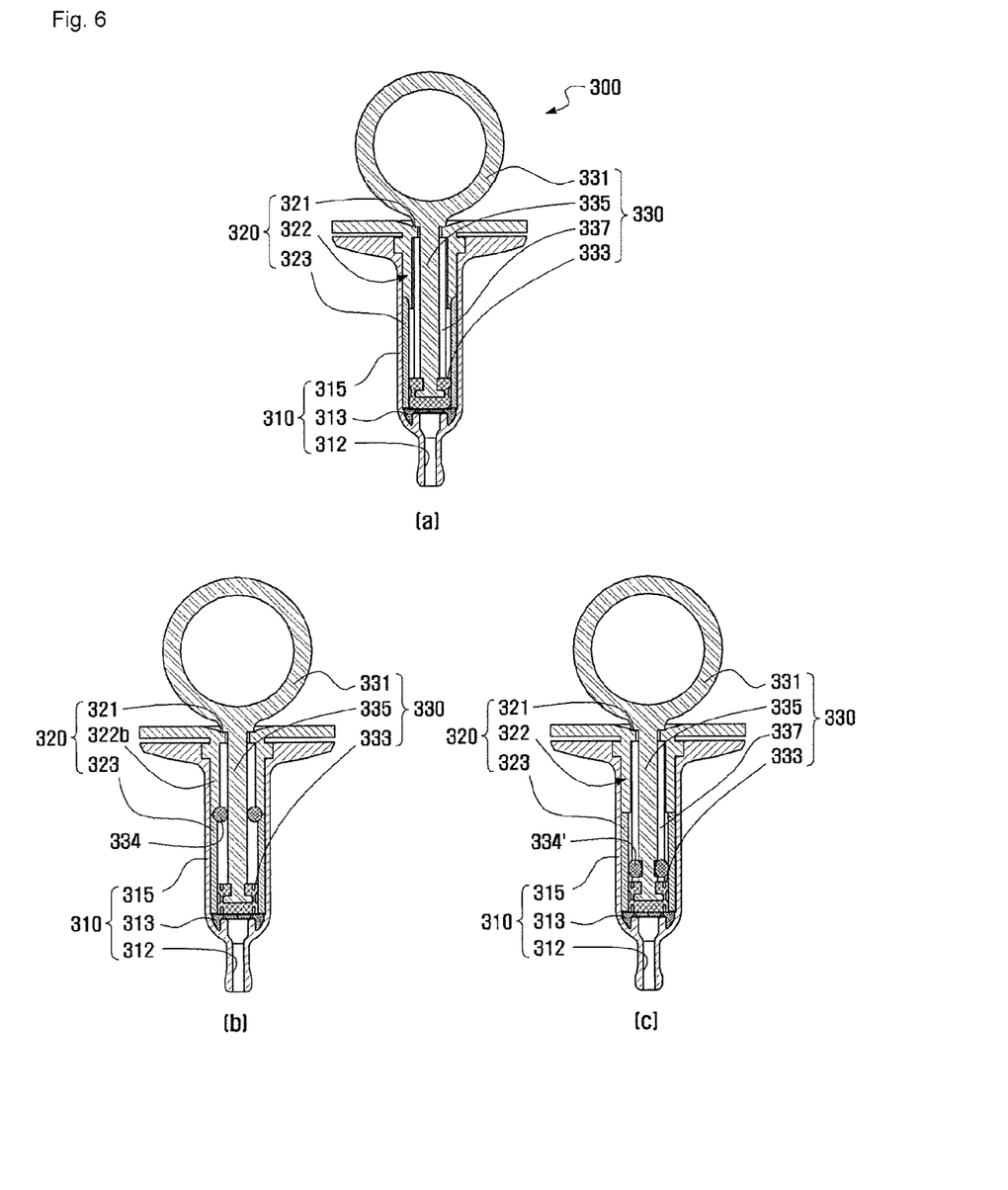
FIG. 6 is a cross-sectional view showing syringe units according to various embodiments of the present disclosure.

FIG. 6 is a cross-sectional view showing syringe units according to various embodiments of the present disclosure. The syringe unit 300 according to the present disclosure may determine the degree of a frictional force which is capable of discharging the solution in the liquid store area 230 at a constant speed, depending on how effectively the piston head 333 maintains a sealed state together with the auxiliary ring member 323. First, in the syringe unit 300 according to an embodiment of the present disclosure, as shown in FIG. 6a, the piston head 333 is made of elastic material so that the piston head 333 may move upwards while keeping a close contact with the auxiliary ring member 323. In addition, similar to the syringe unit 300 according to another embodiment of the present disclosure, the piston head 333 may be made of material such as PE, which may maintain dimension stability and firmly keep a coupling state with the piston rod. In other words, as shown in FIGS. 6b and 6c, the rubber ring member 334, 334' may be installed between the auxiliary ring member 323 and the guide tube 322b or at the outer circumference of the piston rod 335 located above the piston head 333. By doing so, in a state in which the auxiliary ring member 323 and the piston unit 330 maintain a sealed state, a friction force may be generated by moving the piston head 333. In other words, since a frictional force is given so that the piston head 333 may move at a constant speed, it is possible to prevent the content in the syringe unit 300 from bouncing out abruptly.

Figure 7:
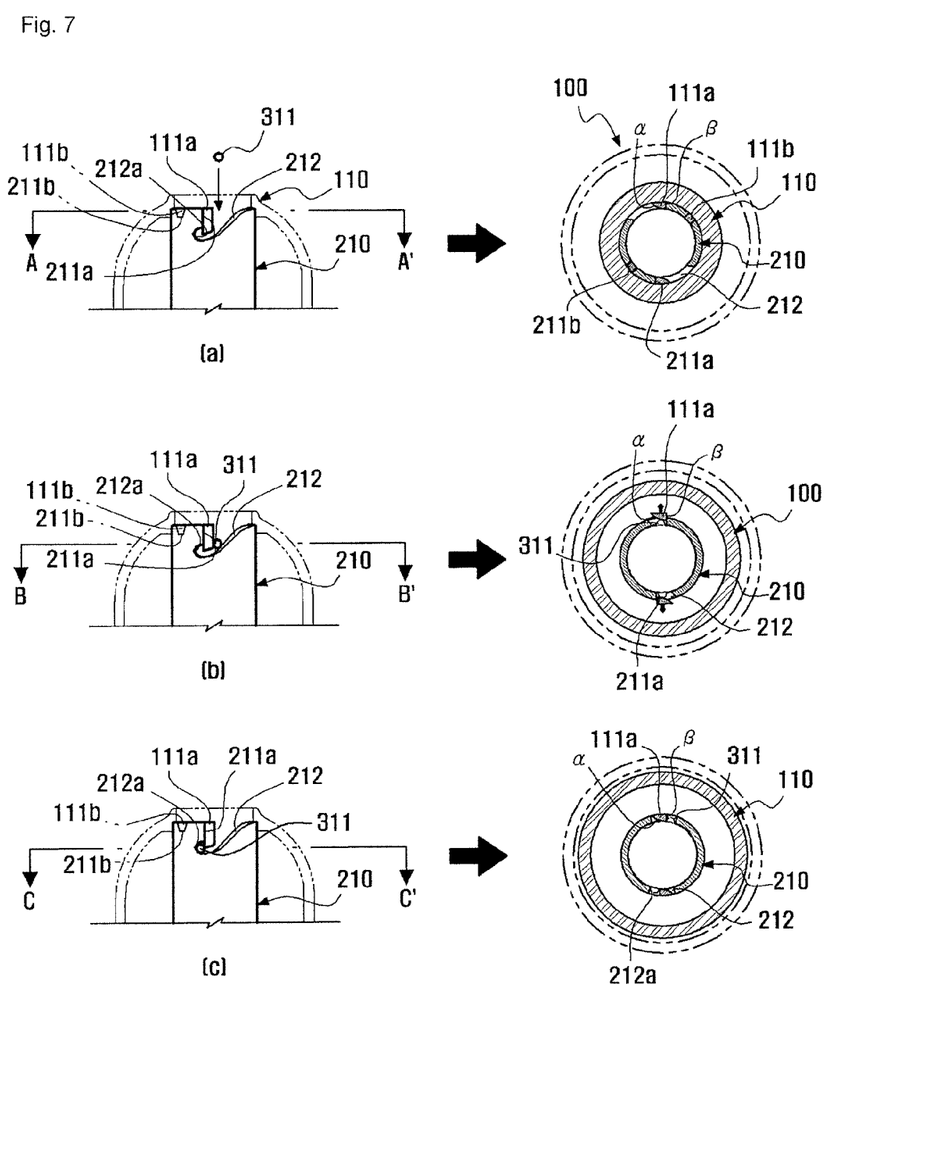
FIG. 7 is a schematic view showing a coupled state of a rotational pressing guide and a guide protrusion according to an embodiment of the present disclosure.

FIG. 7 is a schematic view showing a coupled state of a rotational pressing guide and a guide protrusion according to an embodiment of the present disclosure.

The cylinder chamber 210 in which the syringe unit 300 is inserted may store the syringe unit 300 simply inserted therein, but, as shown in FIG. 7, the rotational pressing guide 212 may be formed at the cylinder chamber 210 so that the syringe unit 300 is fixed to and stored in the cylinder chamber 210. In addition, if the syringe unit 300 is fixed to the cylinder chamber 210, the mounting hole 110 may be covered even though a separate cap is not provided. Therefore, it is possible to prevent alien substances from being introduced into the inner container 200 and the housing 100 or adhered to the syringe unit 300. In addition, since the syringe unit 300 is coupled to the inner container 200, it is possible to prevent the syringe unit 300 from being lost. The rotational pressing guide 212 is formed by cutting with a slope in the longitudinal downward direction from the upper end of the cylinder chamber 210, and a hooking projection 212a is formed at the terminal of the rotational pressing guide 212 so that the guide protrusion 311 may be inserted therein. Here, the first protrusion coupling unit 211a is formed above the hooking projection 212a so that the guide protrusion 311 keeps inserted into the hooking projection 212a. The first protrusion coupling unit 211a is formed by cutting upwards at the upper portion of the hooking projection, and the cut position is located above a point eccentric from the center of the hooking projection toward the rotational pressing guide 212 as shown in FIG. 7a. Since the first protrusion coupling unit 211a is formed at a location eccentric from the hooking projection as described above, the guide protrusion 311 may be stably placed on the hooking projection 212a. The first protrusion 111a is located on the first protrusion coupling unit 211a. Here, the first protrusion 111a makes the guide protrusion 311 placed on the hooking projection 212a not depart from the hooking projection 212a without any external force. The first protrusion 111a includes a coupling surface β contacting the first protrusion coupling unit 211a and a slip surface α oriented to the radial inner side of the housing. Here, a distance between the slip surface α and the syringe unit 300 becomes shorter as being closer to the coupling surface β.

The guide protrusion 311 is coupled to the hooking projection 212a as follows. As shown in FIG. 7b, if the guide protrusion 311 moving downwards along the rotational pressing guide 212 contacts the slip surface α of the first protrusion 111a, the terminal of the first protrusion 111a spaced apart from the housing 100 elastically moves outwards, namely outwards in a radial direction of the cylinder chamber 210. If the guide protrusion 311 moving while pushing the first protrusion 111a moves to the hooking projection 212a as shown in FIG. 7c, the force pushing the slip surface α of the first protrusion 111a is removed, and the first protrusion 111a is restored to its original location. At this time, the guide protrusion 311 is placed on the hooking projection 212a while contacting the planar coupling surface β. Therefore, the guide protrusion 311 placed on the hooking projection 212a may not depart from the hooking projection 212a without any external force. In other words, the coupled state between the cylinder unit 310 and the cylinder chamber 210 may be maintained more firmly.

Figure 8:
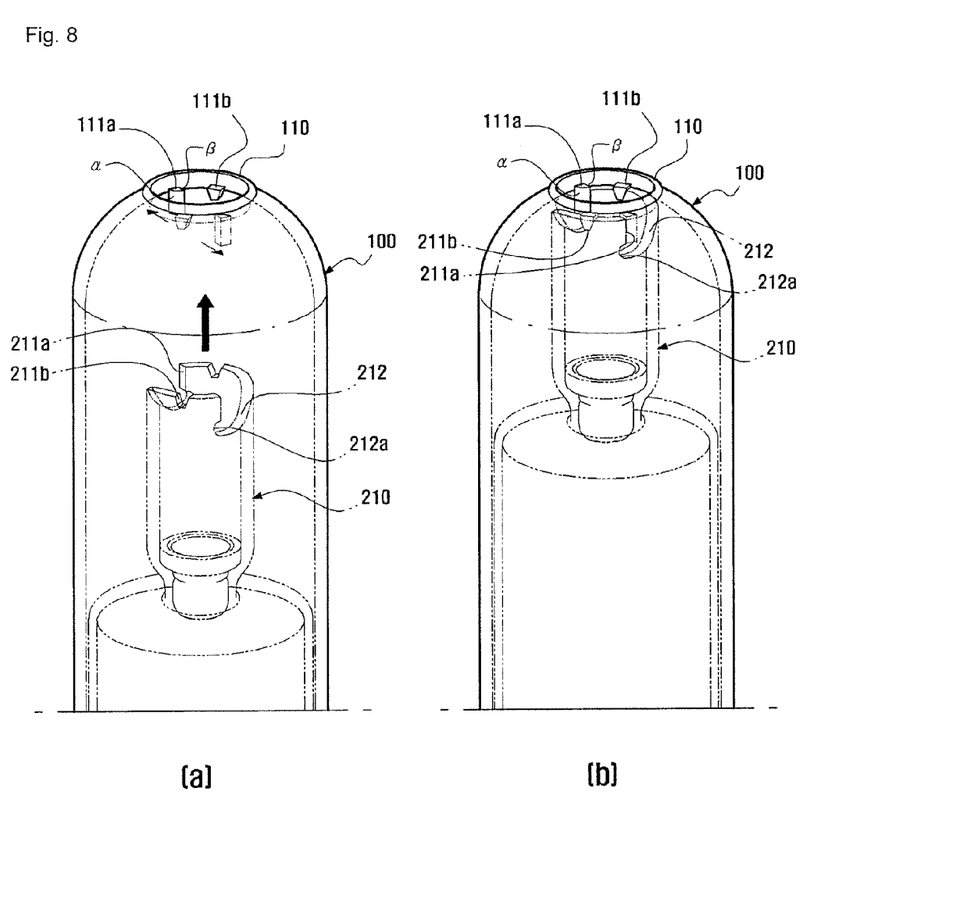
FIG. 8 is a perspective view showing a coupling method of an inner container and a housing according to an embodiment of the present disclosure.

FIG. 8 is a perspective view showing a coupling method of an inner container and a housing according to an embodiment of the present disclosure.

The protrusion and the protrusion coupling unit may have various shapes so that the inner container 200 and the housing 100 are fixed in a coupled state. However, the protrusion and the protrusion coupling unit may be shaped as in the liquid container having a vacuum pumping device according to an embodiment of the present disclosure. First, the protrusion includes a first protrusion 111a and a second protrusion 111b, and the protrusion coupling unit includes a first protrusion coupling unit 211a and a second protrusion coupling unit 211b respectively coupled with the first protrusion 111a and the second protrusion 111b. In other words, as shown in FIG. 8, the first protrusion coupling unit 211a is formed to contact the coupling surface β which is one surface of the first protrusion 111a so that the slip surface α of the first protrusion 111a does not contact the inner container 200. Therefore, the first protrusion 111a may be configured to help the coupling of the guide protrusion 311. In addition, the second protrusion coupling unit 211b is formed to contact both sides of the second protrusion 111b. In this case, if the second protrusion 111b formed in the housing 100 is inserted into the second protrusion coupling unit 211b formed at the inner container 200, it is possible to prevent the inner container 200 from rotating in the housing 100. If the inner container 200 and the housing 100 are coupled as described above, the syringe unit 300 may be fixed in the inner container 200 and simultaneously the inner container 200 may be coupled in a fixed state in the housing 100.

Figure 9:
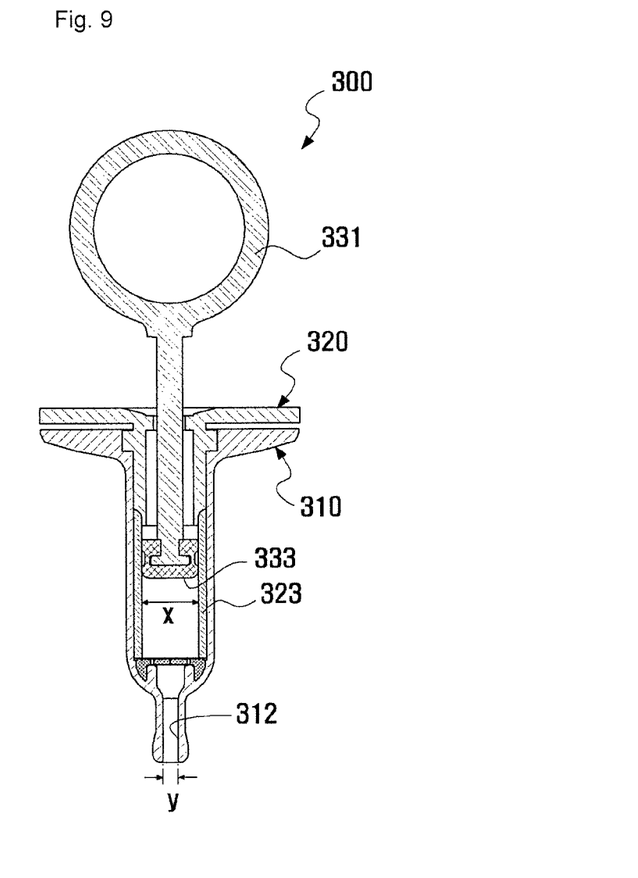
FIG. 9 is a schematic cross-sectional view showing a syringe unit according to an embodiment of the present disclosure.

FIG. 9 is a schematic cross-sectional view showing a syringe unit according to an embodiment of the present disclosure.

The syringe unit 300 according to the present disclosure may set a ratio of an inner diameter x of the coupling unit 320 and an inner diameter y of the inlet/outlet tube 312 in order to discharge the solution in the liquid store area 230 more easily. In other words, the inner diameter x of the auxiliary ring member 323 serving as the coupling unit 320 through which a solution flows in may be designed to be one to ten times of the inner diameter y of the inlet/outlet tube 312, so that the solution may easily flow into the syringe unit 300. The liquid container having a vacuum pumping device according to the present disclosure may discharge solutions of various viscosities to the outside. If the inner diameter y of the inlet/outlet tube 312 is identical to the inner diameter x of the auxiliary ring member 323, a syringe solution may be easily sucked. However, if the inner diameter y of the inlet/outlet tube 312 is greater than the inner diameter x of the auxiliary ring member 323, the solution to be sucked may not be minutely controlled. In other words, a greater amount of solution than required is discharged from the liquid store area 230. Therefore, for controlling this, the moving distance of the piston unit 330 should be controlled extremely minutely, which wastes unnecessary time when sucking the solution to the syringe unit 300. In addition, if the inner diameter x of the auxiliary ring member 323 is greater than ten times of the inner diameter y of the inlet/outlet tube 312, even though the amount of solution sucked by the syringe unit 300 may be minutely controlled, if the solution sucked has a high viscosity, the piston unit 330 may not be moved upwards. Therefore, the inner diameter x of the auxiliary ring member 323 may be designed to be one to ten times of the inner diameter of the inlet/outlet tube 312.

Simple changes or modifications of the present disclosure may be easily implemented by those having ordinary skill in the art, and these changes or modifications may be regarded as being included in the scope of the present disclosure.

The invention claimed is:

1. A liquid container having a vacuum pumping device, comprising:
a housing having a lower portion which is opened by means of an opening or closing control to be exposed to the atmosphere and an upper portion having a mounting hole so that a space is formed therein;

an inner container having a cylinder chamber provided at an upper portion thereof to allow a liquid to flow in or out and a liquid store area connected to a lower portion of the cylinder chamber to change a volume according to an amount of liquid therein, the cylinder chamber being coupled to the mounting hole of the housing so that the inner housing is detachably mounted in the housing for refilling;

a syringe unit coupled to or separated from the cylinder chamber to suck the liquid from the inner container and discharge the sucked liquid outwards; and an elastic cap mounted to the cylinder chamber, the elastic cap being closed in advance when the syringe unit is inserted into the cylinder chamber and opened later when the syringe unit sucks the liquid after the syringe unit is inserted into the cylinder chamber, so that the liquid is discharged while keeping a sealed state.

2. The liquid container having a vacuum pumping device according to claim 1, wherein the syringe unit is coupled to or separated from the cylinder chamber by means of a turn of 90° to 180°.

3. The liquid container having a vacuum pumping device according to claim 1,
wherein a protrusion is formed in a space of the mounting hole of the housing,
wherein a protrusion coupling unit shaped corresponding to the protrusion is formed at the upper end of the cylinder chamber, and
wherein the cylinder chamber is fixed in the housing by means of coupling between the protrusion of the housing and the protrusion coupling unit of the cylinder chamber.

4. The liquid container having a vacuum pumping device according to claim 3,
wherein the cylinder chamber includes a rotational pressing guide formed by cutting from the upper end of the cylinder chamber with a slope with respect to the longitudinal direction thereof, the rotational pressing guide having a hooking projection formed at a lower terminal thereof to prevent the syringe unit from bouncing in the longitudinal direction, and
wherein a guide protrusion guided by the rotational pressing guide is further formed at the outer circumference of the syringe unit.

5. The liquid container having a vacuum pumping device according to claim 4,
wherein the protrusion coupling unit is formed in plural at the cylinder chamber and includes a first protrusion coupling unit located above a point eccentric from the center of the hooking projection toward the rotational pressing guide,
wherein the protrusion is connected in plural to the housing and includes a first protrusion contacting the first protrusion coupling unit, and
wherein the first protrusion includes a coupling surface contacting the first protrusion coupling unit and a slip surface oriented toward the housing, and the slip surface is formed so that a distance to the syringe unit is shorter as being closer to the coupling surface.

6. The liquid container having a vacuum pumping device according to claim 4, wherein the syringe unit includes:
a cylinder unit having the guide protrusion formed at the outer circumference of a tube-shaped cylinder body;
a piston unit mounted in the cylinder unit; and
a coupling unit formed between the piston unit and the cylinder unit, wherein the piston unit has a piston rod vertically movable along the piston guide unit and a piston head coupled to the lower end of the piston rod.

7. The liquid container having a vacuum pumping device according to claim 6, wherein the cylinder unit includes:
the cylinder body;
an inlet/outlet tube connected to one end of the cylinder body and having a diameter smaller than or equal to that of the cylinder body;
a hydraulic pressure control valve coupled to one end of the cylinder body to control a hydraulic pressure of the liquid so that the liquid flowing into the cylinder body is not abruptly discharged out; and
the guide protrusion formed at the outer circumference of the cylinder body,
wherein the hydraulic pressure control valve is made of elastic material with a plate shape and has a first inlet/outlet hole formed with an arc shape at a location spaced apart from the center of the hydraulic pressure control valve and a second inlet/outlet hole formed at the center of the hydraulic pressure control valve.

8. The liquid container having a vacuum pumping device according to claim 7,
wherein a barrier is connected to one end of the cylinder body to protrude in the longitudinal direction of the cylinder unit, and
wherein the first inlet/outlet hole is located at an upper portion of the barrier.

9. The liquid container having a vacuum pumping device according to claim 7,
wherein an inner diameter of the cylinder body is one to ten times of an inner diameter of the inlet/outlet tube.

10. The liquid container having a vacuum pumping device according to claim 6,
wherein a grip having a diameter greater than the piston rod is connected to the upper end of the piston rod, and
wherein a vertical length of the grip is 15 mm to 35 mm.

11. The liquid container having a vacuum pumping device according to claim 6, wherein the coupling unit includes:
a piston guide for limiting an upward movement range of the piston unit; and
an auxiliary ring member located at a lower portion of the piston unit.

12. The liquid container having a vacuum pumping device according to claim 11,
wherein the piston unit is inserted into the piston guide and the auxiliary ring member,
wherein an inner diameter of the piston guide is smaller than an outer diameter of the piston head, and
wherein an outer diameter of the piston head vertically sliding in the auxiliary ring member is greater than an inner diameter of the lower end of the auxiliary ring member.

13. The liquid container having a vacuum pumping device according to claim 11, wherein the piston guide includes:
a flat flange having a piston insert hole; and
a guide tube vertically connected downwards from the piston insert hole of the flange so that the piston unit is inserted therein.

14. The liquid container having a vacuum pumping device according to claim 13,
wherein a guide part is formed at the guide tube to protrude into the guide tube,
wherein a piston guide groove is concavely formed at the outer circumference of the piston unit in the vertical longitudinal direction, and wherein the guide part is inserted and coupled into the piston guide groove.

15. The liquid container having a vacuum pumping device according to claim 13, wherein a rubber ring member for sealing the auxiliary ring member is coupled between the lower end of the guide tube and the auxiliary ring member.

16. The liquid container having a vacuum pumping device according to claim 13, wherein a rubber ring member for sealing the auxiliary ring member is coupled to the outer circumference of the piston unit.

17. The liquid container having a vacuum pumping device according to claim 1,
wherein the elastic cap includes an insertion body into which a terminal of the syringe unit is inserted, and a channel opening/closing hole formed through the bottom surface of the insertion body, and
wherein a slit is formed by cutting at the channel opening/closing hole so that the slit is opened when being pressed by the syringe unit.

18. The liquid container having a vacuum pumping device according to claim 1,
wherein the elastic cap includes an insertion body into which a terminal of the syringe unit is inserted, and a channel opening/closing hole formed through the bottom surface of the insertion body, and
wherein the channel opening/closing hole has a membrane protruding upwards with a slant from the bottom surface of the elastic cap, and a cut portion formed through the membrane at an uppermost end of the membrane.

19. The liquid container having a vacuum pumping device according to claim 18,
wherein an elastic cap placing portion is provided at a lower portion of the cylinder chamber located in the liquid store area so that the elastic cap is mounted thereto, and
wherein a channel control protrusion protruding upwards from the bottom surface and a discharge tube formed through the bottom surface of the elastic cap placing portion are provided at the bottom surface of the elastic cap placing portion.

20. The liquid container having a vacuum pumping device according to claim 19,
wherein the bottom surface of the insertion body is located at an upper portion of the discharge tube, and the elastic cap and the elastic cap placing portion are coupled so that the channel control protrusion is inserted into the channel opening/closing hole, and
wherein the channel control protrusion is formed spaced apart from the membrane.

* * * * *